(12) United States Patent
Philippe et al.

(10) Patent No.: US 6,255,332 B1
(45) Date of Patent: Jul. 3, 2001

(54) USE OF OXAZOLIDINONE DERIVATIVES AS ANTI-PENETRATING AGENTS IN A COSMETIC AND/OR DERMATOLOGICAL COMPOSITION

(75) Inventors: Michel Philippe, Wissous; Rémy Tuloup, Paris; Jean-Luc Morancais, Ozoir la Ferriere, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 08/949,822

(22) Filed: Oct. 14, 1997

(30) Foreign Application Priority Data

Oct. 14, 1996 (FR) .................................... 96 12509

(51) Int. Cl.⁷ .............................. A61K 31/42; A61K 7/00
(52) U.S. Cl. .......................... 514/376; 424/400; 424/401
(58) Field of Search ............................................. 514/376

(56) References Cited

U.S. PATENT DOCUMENTS

| 4,382,765 | 5/1983 | Möller et al. . |
| 4,837,026 | * 6/1989 | Rajakhyaksha ...................... 514/788 |
| 4,960,771 | * 10/1990 | Rajakhyaksha ...................... 514/376 |

FOREIGN PATENT DOCUMENTS

| 0 391 273 | 10/1990 | (EP) . |
| 2 379 283 | 9/1978 | (FR) . |
| WO 90/00407 | 1/1990 | (WO) . |

* cited by examiner

*Primary Examiner*—Shelley A. Dodson
(74) *Attorney, Agent, or Firm*—Finnegan, Henderson, Farabow, Garrett & Dunner, L.L.P.

(57) ABSTRACT

The use of oxazolidinone derivatives in a composition for topical application, especially a cosmetic or dermatological composition, in particular as anti-penetrating agents. These derivatives make it possible especially to prevent the penetration of active agents which are compatible with the skin, the hair and/or mucous membranes, and thus to reduce, or even eliminate altogether, the side effects of these active agents without decreasing their efficacy. Thus, the cosmetic or dermatological compositions containing such active agents make it possible to soften the skin, mucous membranes and the hair.

36 Claims, No Drawings

USE OF OXAZOLIDINONE DERIVATIVES AS ANTI-PENETRATING AGENTS IN A COSMETIC AND/OR DERMATOLOGICAL COMPOSITION

The invention relates to the use of oxazolidinone derivatives, in particular as anti-penetrating agents, in a composition for topical application intended especially to treat human facial and/or body skin, including the scalp, the hair and/or mucous membranes.

It is known to introduce active agents into cosmetic and/or dermatological compositions in order to provide treatments specific to the skin, mucous membranes or the hair, for example in order to combat the drying out, ageing or pigmentation of the skin, to treat acne or certain skin diseases (eczema, psoriasis), to combat problems of excess weight, to promote restructuring or cell renewal of the skin, to protect the skin or hair against the sun's rays, to cleanse or dye the skin or the hair, or alternatively to make up the skin.

Unfortunately, certain active agents have the drawback of causing stinging, itching or tightness after they have been applied, which may lead to considerable discomfort. Users with sensitive skin are thus often prevented from using these compounds.

A certain number of solutions have been proposed in order to overcome these drawbacks. In particular, document WO-A-93/21904 envisages using a water-soluble polyurethane in order to reduce the irritation caused by retinoic acid. Moreover, it is known to use certain polymer derivatives such as polyvinylpyrrolidone (see FR-A-2,224,126) or polyoxyethylenated polysiloxanes (see EP-A-266,921) in order to decrease the skin irritation. In addition, it is known from document EP-A-391,274 to use acrylic polymer coderivatives in solution in order to prevent the penetration of certain irritant products.

The inventors have found, surprisingly, that certain oxazolidinone derivatives have the property of reducing, or even eliminating altogether, the penetration of active agents while at the same time not decreasing their efficacy. This property may be exploited in order to decrease, or even eliminate altogether, the undesirable side effects introduced by these active agents, in particular active agents with an irritant or sensitizing side effect, that is to say agents having a potential for secondary risks. This property is all the more surprising since it is contradictory to what is described in the prior art. Indeed, document U.S. Pat. No. 4,960,771 describes the use of oxazolidinone derivatives in order to improve the penetration of physiologically active agents.

The subject of the invention is the use of at least one oxazolidinone derivative of formula (I):

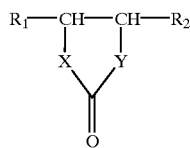

in which:
$R_1$ represents a linear or branched, saturated or unsaturated hydroxyalkyl radical having from 6 to 27 carbon atoms,
$R_2$ represents hydrogen or a linear or branched, saturated or unsaturated alkyl or hydroxyalkyl radical having from 1 to 7 carbon atoms,
X and Y, which are different from each other, represent —$NR_3$ or an oxygen atom, $R_3$ representing hydrogen or a linear or branched, saturated or unsaturated alkyl or hydroxyalkyl radical having from 1 to 8 carbon atoms, in a cosmetic composition or for the manufacture of a dermatological composition containing a physiologically acceptable medium, in order to reduce or prevent the penetration of at least one active agent which is compatible with the skin, the hair and/or mucous membranes.

When the active agent can be potentially irritant or sensitizing, the presence of an oxazolidinone derivative according to the invention makes it possible to prevent the penetration of this active agent and thereby the irritation and/or sensitization of the composition containing it, without decreasing the efficacy of the active agent. A non-irritant composition which may be applied topically to human facial and/or body skin, the hair and/or mucous membranes may thus be obtained.

Thus, the subject of the present invention is also the use of at least one oxazolidinone derivative of formula (I)

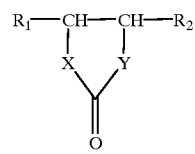

in which:
$R_1$ represents a linear or branched, saturated or unsaturated hydroxyalkyl radical having from 6 to 27 carbon atoms,
$R_2$ represents hydrogen or a linear or branched, saturated or unsaturated alkyl or hydroxyalkyl radical having from 1 to 7 carbon atoms,
X and Y, which are different from each other, represent —$NR_3$ or an oxygen atom, $R_3$ representing hydrogen or a linear or branched, saturated or unsaturated alkyl or hydroxyalkyl radical having from 1 to 8 carbon atoms, in a cosmetic composition or for the manufacture of a dermatological composition containing a physiologically acceptable medium, in order to reduce or prevent the appearance of the irritant or sensitizing nature of at least one active agent having an irritant or sensitizing side effect.

The active agent may be found either in the same composition as the derivative of formula (I) or in another composition which is applied at the same time or after the composition containing the derivative of formula (I) is applied, or alternatively just before it is applied. Preferably, the active agent and the derivative of formula (I) are in the same composition.

The derivatives of formula (I) may be prepared conventionally by reaction of ethylene carbonate with an aminoalkane polyol at a temperature above 60° C. The synthesis may lead to the production of several positional isomers and stereoisomers.

The preferred derivatives of formula (I) are those in which, in formula (I), X represents —NH—, Y represents oxygen, $R_1$ represents a saturated hydroxyalkyl radical having from 12 to 20 carbon atoms and $R_2$ represents hydrogen or a saturated alkyl or hydroxyalkyl radical having from 1 to 3 carbon atoms.

As preferred derivatives of formula (I), mention may be made, for example, of 4-(1-hydroxyhexadecyl)-2-oxazolidinone, 4-pentadecyl-5-hydroxymethyl-2-oxazolidinone, 4-(1,2-dihydroxyhexadecyl)-2-oxazolidinone, 4-(1-hydroxypentadecyl)-5-hydroxymethyl-2-oxazolidinone, their stereoisomers and their mixtures.

The composition containing the derivative of formula (I) highly preferably contains a physiologically acceptable medium, that is to say one which is compatible with the skin, including the scalp, the hair and/or mucous membranes.

The invention applies to any active agent which is compatible with the skin, the hair and/or mucous membranes. As examples of active agents to which the invention applies more particularly, mention may be made of exfoliants, that is to say active agents having, in particular, a keratolytic and/or comedolytic property, sunscreens, dyestuffs, preserving agents, surfactants and fragrances.

As active agents, mention may be made more particularly of α-hydroxy acids (glycolic acid, lactic acid, malic acid, citric acid, tartaric acid or mandelic acid), β-hydroxy acids (salicylic acid and its derivatives such as 5-n-octanoylsalicylic acid, 5-n-decanoylsalicylic acid, 5-n-dodecanoylsalicylic acid, 5-n-octylsalicylic acid, 5-n-heptyloxysalicylic acid and 4-n-heptyloxysalicylic acid), α-keto acids, β-keto acids, retinoids (retinol, retinoic acid, retinal and their derivatives), anthralins (dioxyanthranol), anthranoids, peroxides (in particular benzoyl peroxide), Minoxidil, antimetabolites such as 5-fluorouracil, hair tints or dyes (para-phenylenediamine and its derivatives, aminophenols), perfuming alcoholic solutions (fragrances, eaux de toilette, aftershave and deodorants), antiperspirants (certain aluminium salts), hair-removing or permanent-waving active agents (thiols), depigmenting agents (hydroquinone), pigments and chemical screening agents.

Depending on the amount used and the skin-sensitivity of the user, these active agents may prove to be more or less irritant or sensitizing.

The amount of oxazolidinone derivative of formula (I) in the composition may range, for example, from 0.05 to 20%, and more particularly from 0.1 to 5%, by weight relative to the total weight of the composition. In the presence of active agent, this amount depends in particular on the amount of active agent in the composition.

Moreover, the amount of active agent may vary within a wide range depending on the nature and/or function of the active agent. This amount may range, for example, from 0.001 to 20% by weight relative to the total weight of the composition.

The compositions containing the oxazolidinone derivative of formula (I) and/or the active agent may be in any form, preferably a pharmaceutical form, which is normally suitable for topical application, and, for example, in the form of an aqueous, alcoholic, aqueous-alcoholic or oily solution, an aqueous or oily gel, a solid anhydrous composition, a dispersion of the lotion or serum type, an emulsion of the water-in-oil (W/O), oil-in-water (O/W) or multiple (W/O/W or O/W/O) type, a microemulsion or a vesicle dispersion of ionic and/or nonionic type. These compositions are prepared according to the usual methods.

They may also be used for the hair in the form of aqueous, alcoholic or aqueous-alcoholic solutions, or in the form of creams, gels, emulsions or foams or alternatively in the form of aerosol compositions also containing a propellant under pressure.

The amounts of the various constituents of the compositions according to the invention are those used conventionally in the fields considered.

These compositions in particular constitute cleansing, protecting, treatment or care creams for the face, the hands, the feet or the body (for example day creams, night creams, make-up-removing creams, foundation creams and antisun creams), make-up products such as foundations, blushers or lipsticks, make-up-removing milks, protective body milks, bodycare milks, antisun milks, skincare lotions, gels or mousses, such as cleansing lotions, antisun lotions, artificial tanning lotions, bath compositions, deodorizing compositions containing a bactericidal agent, aftershave gels or lotions, hair-removing creams, insect-repellent compositions and pain-relief compositions.

The derivative(s) of formula (I) may also be incorporated into various haircare compositions, and especially shampoos, which may be antidandruff shampoos, hairsetting lotions, treating lotions, styling creams or gels, dye compositions (in particular oxidation dye compositions) which may be in the form of dyeing shampoos, hair restructuring lotions, permanent-wave compositions (in particular compositions for the first stage of a permanent-wave operation), lotions or gels to combat hair loss, etc.

The compositions of the invention may also be for buccodental use, for example a toothpaste. In this case, the compositions may contain adjuvants and additives that are common for compositions for oral use and, in particular, surfactants, thickeners, wetting agents, polishing agents such as silica, various active ingredients such as fluorides, in particular sodium fluoride, and optionally sweeteners such as sodium saccharinate.

The compositions according to the invention may also comprise solid preparations which constitute cleansing soaps or bars.

The compositions may also be packaged in the form of an aerosol composition also containing a propellant under pressure.

When the composition of the invention is an emulsion, the proportion of the fatty phase may range preferably from 5 to 80%, and more preferably from 5 to 50%, by weight relative to the total weight of the composition. The fatty substances, the emulsifiers and the coemulsifiers used in the composition in emulsion form are chosen from those used conventionally in the cosmetic and dermatological fields. The emulsifier and coemulsifier are present, in the composition, in a proportion ranging preferably from 0.3 to 30%, and more preferably from 0.5 to 20%, by weight relative to the total weight of the composition. The emulsion may also contain lipid vesicles.

In a known manner, the composition of the invention may also contain adjuvants that are common in the cosmetic and dermatological fields, such as hydrophilic or lipophilic gelling agents, hydrophilic or lipophilic active agents, preserving agents, antioxidants, solvents, fragrances, fillers, screening agents, odour absorbers and dyestuffs. The amounts of these various adjuvants are those used conventionally in the fields considered, for example, from 0.01 to 30% by weight relative to the total weight of the composition. Depending on their nature, these adjuvants may be introduced into the fatty phase, into the aqueous phase and/or into the lipid spherules.

As fatty substances which may be used in the invention, mention may be made of oils and more particularly mineral oils, oils of plant origin, oils of animal origin, synthetic oils, silicone oils and fluoro oils. Fatty alcohols, fatty acids and waxes may also be used as fatty substances.

As hydrophilic gelling agents, mention may be made of carboxyvinyl polymers (carbomer), acrylic copolymers such as acrylate/alkyl acrylate copolymers, polyacrylamides, polysaccharides such as hydroxypropylcellulose, natural gums and clays, and, as lipophilic gelling agents, mention may be made of modified clays such as bentones, metal salts of fatty acids such as aluminium stearates, hydrophobic silica, polyethylenes and ethylcellulose.

Other characteristics and advantages of the invention will emerge more clearly from the examples, given by way of non-limiting illustration, which follow.

The example which follows illustrates the process for the preparation of the derivatives in accordance with the invention.

EXAMPLE 1

Preparation of a Mixture of 4-(1-hydroxyhexadecyl)-2-oxazolidinone and 4-pentadecyl-5-hydroxymethyl-2-oxazolidinone 10 g of 2-amino-1,3-octadecanediol ($3.31 \times 10^{-2}$ mol) are reacted with 3.2 g of ethylene carbonate ($3.64 \times 10^{-2}$ mol) at 110° C. for 48 hours. The mixture is then recrystallized from 200 ml of heptane. 10.2 g (yield: 94%) of a mixture of 4-(1-hydroxyhexadecyl)-2-oxazolidinone and 4-pentadecyl-5-hydroxymethyl-2-oxazolidinone are obtained in the form of a white powder having a melting point of 79° C.

| | Elemental analysis | | | |
|---|---|---|---|---|
| | C | H | N | O |
| Calculated | 69.68 | 11.39 | 4.28 | 14.66 |
| Found | 69.14 | 11.57 | 4.21 | 15.13 |

The $^1$H NMR and the mass of the product obtained are in accordance with the expected structure.

EXAMPLE 2

Test

The anti-penetrating activity of the derivatives of formula (I) was evaluated on a model of cell membrane comprising hydrated dipalmitoylphosphatidylcholine. An increase in the phase transition temperature of the membrane reflects an increase in the cohesion of the membrane, resulting in reduced penetration of this membrane by active agents.

Table 1 shows the phase transition temperature values of dipalmitoylphosphatidylcholine (DPPC) alone, compared with those of this same lipid combined with a mixture of two isomeric derivatives of formula (I), corresponding to Example 1, that is to say 4-(1-hydroxyhexadecyl)-2-oxazolidinone and its positional isomer, 4-pentadecyl-5-hydroxymethyl-2-oxazolidinone. The compositions are placed in water to 50% and characterized by differential thermal analysis with heating ranging from 1° C. to 110° C. at a rate of 2° C./min.

TABLE 1

| | Transition temperatures in °C. | |
|---|---|---|
| Molar compositions | start | maximum |
| DPPC | 40.6 ± 0.1 | 41.8 ± 0.1 |
| DPPC/mixture of Example 1 (90/10) | 41.5 ± 0.1 | 42.9 ± 0.1 |
| DPPC/mixture of Example 1 (75/25) | 45.0 ± 0.2 | 47 ± 0.4 |
| DPPC/mixture of Example 1 (50/50) | 48.2 ± 0.2 | 49.4 ± 0.3 |

The results of Table 1 show a clear increase in the phase transition temperatures (start and maximum) of dipalmitoylphosphatidylcholine when it is combined with the compounds according to the invention, thereby demonstrating reduced penetration of the cell membrane made of dipalmitoylphosphatidylcholine.

In the same study, N-dodecyl-ε-caprolactam (azone) and 4-decyl-2-oxazolidinone (Example 1 of U.S. Pat. No. 4,960,771), in contrast with the mixture of Example 1 herein, lower the phase transition temperature of DPPC significantly (maximum phase transition temperatures below 40° C.) for 50% DPPC mixtures in combination with either of these compounds (see Table 2).

TABLE 2

| | Transition temperatures in ° C. | |
|---|---|---|
| Molar compositions | start | maximum |
| DPPC | 40.6 ± 0.1 | 41.8 ± 0.1 |
| DPPC/N-dodecyl-ε-caprolactam (50/50) | 15.6 ± 0.4 | 30.1 ± 0.0 |
| DPPC/4-decyl-2-oxazolidinone 50/50 | 10.4 ± 0.0 | 29.4 ± 0.2 |

These results show that derivatives of the prior art lower the phase transition temperature and are incapable of preventing the penetration of active agents.

The examples which follow illustrate the cosmetic or dermatological compositions according to the invention. The amounts are given as a percentage by weight.

EXAMPLE 3

Vesicle Dispersion

| | |
|---|---|
| mixture of 4-(1-hydroxyhexadecyl)-2-oxazolidinone and 4-pentadecyl-5-hydroxymethyl-2-oxazolidinone | 2.14% |
| cholesterol | 2.14% |
| sodium dicetyl phosphate | 0.48% |
| preserving agent | 0.24% |
| glycerol (wetting agent) | 2.91% |
| water | qs 100% |

The dispersion is obtained by dissolving the lipids (mixture of 4-(1-hydroxyhexadecyl)-2-oxazolidinone and 4-pentadecyl-5-hydroxymethyl-2-oxazolidinone+cholesterol+sodium dicetyl phosphate) in solvent ($CH_2Cl_2$), evaporation of the solvent, and dispersion of the lipids in the aqueous phase containing the water, glycerol and the preserving agent.

A dispersion which prevents penetration of active agent when it is applied to the skin is obtained.

EXAMPLE 4

Care Composition Containing a Vesicle Dispersion

| | |
|---|---|
| mixture of 4-(1-hydroxyhexadecyl)-2-oxazolidinone and 4-pentadecyl-5-hydroxymethyl-2-oxazolidinone | 2.25% |
| cholesterol | 2.24% |
| sodium dicetyl phosphate | 0.50% |
| preserving agent | 0.24% |
| lactic acid | 1.91% |
| water | qs 100% |

The dispersion is obtained by dissolving the lipids (mixture of 4-(1-hydroxyhexadecyl)-2-oxazolidinone and 4-pentadecyl-5-hydroxymethyl-2-oxazolidinone+cholesterol+sodium dicetyl phosphate) in solvent ($CH_2Cl_2$), evaporation of the solvent, and dispersion of the lipids in the aqueous phase containing the water, lactic acid and the preserving agent.

A dispersion which is able to make the skin smooth without irritating it is obtained.

We claim:

1. A process for the preparation of a cosmetic or dermatological composition, comprising the step of including in said composition at least one anti-penetrating agent, said anti-penetrating agent being an oxazolidinone compound of formula (I):

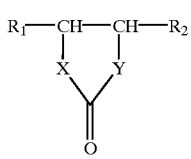

wherein:
- $R_1$ represents a linear or branched, saturated or unsaturated hydroxyalkyl radical having from 6 to 27 carbon atoms,
- $R_2$ represents hydrogen or a linear or branched, saturated or unsaturated alkyl or hydroxyalkyl radical having from 1 to 7 carbon atoms, and
- X and Y, which are different from each other, represent —$NR_3$ or an oxygen atom, $R_3$ representing hydrogen or a linear or branched, saturated or unsaturated alkyl or hydroxyalkyl radical having from 1 to 8 carbon atoms wherein said at least one anti-penetrating agent is included in said composition in an amount effective for, and for the purpose of reducing or preventing penetration into the skin, hair or mucous membrane of said at least one active agent.

2. A process for the preparation of a cosmetic or dermatological composition containing a physiologically acceptable medium, comprising the step of including in said composition at least one anti-penetrating agent, said anti-penetrating agent being an oxazolidinone compound of formula (I):

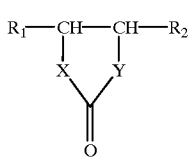

wherein:
- $R_1$ represents a linear or branched, saturated or unsaturated hydroxyalkyl radical having from 6 to 27 carbon atoms,
- $R_2$ represents hydrogen or a linear or branched, saturated or unsaturated alkyl or hydroxyalkyl radical having from 1 to 7 carbon atoms, and
- X and Y, which are different from each other, represent —$NR_3$ or an oxygen atom, $R_3$ representing hydrogen or a linear or branched, saturated or unsaturated alkyl or hydroxyalkyl radical having from 1 to 8 carbon atoms, wherein said at least one anti-penetrating agent is included in said composition in an amount effective for, and for the purpose of, reducing or preventing the appearance of the irritant or sensitizing nature of at least one active agent having an irritant or sensitizing side effect, and wherein said at least one active agent and said at least one anti-penetrating agent may be present as separate components of said composition, said separate components being combined together at about the time of application of said composition to said skin, hair, and/or mucous membranes.

3. A process according to claim 1 wherein X represents —NH—, Y represents oxygen, $R_1$ represents a saturated hydroxyalkyl radical having from 12 to 20 carbon atoms and $R_2$ represents hydrogen or a saturated alkyl or hydroxyalkyl radical having from 1 to 3 carbon atoms.

4. A process according to claim 3 wherein said at least one oxazolidinone derivative of formula (I) is selected from 4-(1-hydroxy-hexadecyl)-2-oxazolidinone, 4-pentadecyl-5-hydroxymethyl-2-oxazolidinone, 4-(1,2-dihydroxyhexadecyl)-2-oxazolidinone, 4-(1-hydroxypentadecyl)-5-hydroxymethyl-2-oxazolidinone and the stereoisomers thereof.

5. A process according to claim 1 wherein said at least one active agent is selected from active agents having a keratolytic and/or comedolytic property, sunscreens, dyestuffs, preserving agents, surfactants and fragrances.

6. A process according to claim 1 wherein said at least one active agent is selected from α-hydroxy acids, β-hydroxy acids, α-keto acids, β-keto acids, retinoids, anthralin, anthranoids, peroxides, Minoxidil, antimetabolites, hair tints, hair dyes, perfuming alcoholic solutions, antiperspirants, hair-removing active agents, permanent-waving active agents, depigmenting agents, pigments and chemical screening agents.

7. A process according to claim 1 wherein said at least one oxazolidinone derivative of formula (I) is present in an amount ranging from 0.05 to 20% by weight relative to the total weight of the composition.

8. A process according to claim 7 wherein said at least one oxazolidinone derivative of formula (I) is present in an amount ranging from 0.1 to 5% by weight relative to the total weight of the composition.

9. A process according to claim 1 wherein said at least one active agent is present in an amount ranging from 0.001 to 20% by weight relative to the total weight of the composition.

10. A process according to claim 1 wherein said composition is in the form of a solution, a gel, a dispersion, an emulsion, a microemulsion or a vesicle dispersion of ionic and/or nonionic type.

11. A process according to claim 1 wherein said composition is a cleansing, protective, treatment, care or make-up composition for the skin and/or the hair.

12. A process for alleviating the side effects of an active agent comprising the step of:
applying a composition containing an anti-penetration compound to the skin, hair or mucous membrane, said compound having the formula (I):

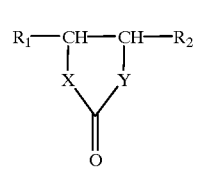

wherein:
- $R_1$ represents a linear or branched, saturated or unsaturated hydroxyalkyl radical having from 6 to 27 carbon atoms,
- $R_2$ represents hydrogen or a linear or branched, saturated or unsaturated alkyl or hydroxyalkyl radical having from 1 to 7 carbon atoms, and
- X and Y, which are different from each other, represent —$NR_3$ or an oxygen atom, $R_3$ representing hydrogen or a linear or branched, saturated or unsaturated alkyl or hydroxyalkyl radical having from 1 to 8 carbon atoms, wherein said anti-penetration compound is included in the composition in amount effective for reducing or preventing penetration of an active agent into the skin, hair or mucous membrane.

13. A process according to claim 12 wherein said composition includes the active agent.

14. A process according to claim 12 further comprising the step of applying a separate composition including the active agent to the skin, hair or mucous membrane.

15. A process according to claim 12 wherein X represents —NH—, Y represents oxygen, $R_1$ represents a saturated hydroxyalkyl radical having from 12 to 20 carbon atoms and $R_2$ represents hydrogen or a saturated alkyl or hydroxyalkyl radical having from 1 to 3 carbon atoms.

16. A process according to claim 12 wherein said at least one oxazolidinone derivative of formula (I) is selected from 4-(1-hydroxyhexadecyl)-2-oxazolidinone, 4-pentadecyl-5-hydroxymethyl-2-oxazolidinone, 4-(1,2-dihydroxyhexadecyl)-2-oxazolidinone, 4-(1-hydroxypentadecyl)-5-hydroxymethyl-2-oxazolidinone and the stereoisomers thereof.

17. A process according to claim 12 wherein said at least one active agent is selected from active agents having a keratolytic and/or comedolytic property, sunscreens, dyestuffs, preserving agents, surfactants and fragrances.

18. A process according to claim 12 wherein said at least one active agent is selected from α-hydroxy acids, β-hydroxy acids, α-keto acids, β-keto acids, retinoids, anthralin, anthranoids, peroxides, Minoxidil, antimetabolites, hair tints, hair dyes, perfuming alcoholic solutions, antiperspirants, hair-removing active agents, permanent-waving active agents, depigmenting agents, pigments and chemical screening agents.

19. A process according to claim 12 wherein said at least one oxazolidinone derivative of formula (I) is present in an amount ranging from 0.05 to 20% by weight relative to the total weight of the composition.

20. A process according to claim 19 wherein said at least one oxazolidinone derivative of formula (I) is present in an amount ranging from 0.1 to 5% by weight relative to the total weight of the composition.

21. A process according to claim 12 wherein said at least one active agent is present in an amount ranging from 0.001 to 20% by weight relative to the total weight of the composition.

22. A process according to claim 12 wherein said composition is in the form of a solution, a gel, a dispersion, an emulsion, a microemulsion or a vesicle dispersion of ionic and/or nonionic type.

23. A process according to claim 12 wherein said composition is a cleansing, protective, treatment, care or make-up composition for the skin and/or the hair.

24. A dermatologic or cosmetic composition comprising an anti-penetrating agent, said anti-penetrating agent being selected from compounds of formula (I):

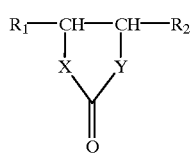

(I)

wherein:

$R_1$ represents a linear or branched, saturated or unsaturated hydroxyalkyl radical having from 6 to 12 carbon atoms, $R_2$ represents hydrogen or a linear or branched, saturated or unsaturated alkyl or hydroxyalkyl radical having from 1 to 7 carbon atoms, and X and Y, which are different from each other, represent —$NR_3$ or an oxygen atom, $R_3$ representing hydrogen or a linear or branched, saturated or unsaturated alkyl or hydroxyalkyl radical having from 1 to 8 carbon atoms, wherein said anti-penetrating agent is included in said composition in an amount effective for reducing or preventing penetration into the skin, hair or mucous membrane of at least one active agent.

25. A dermatologic or cosmetic composition according to claim 24 further comprising at least one active agent.

26. A composition according to claim 24 wherein X represents —NH—, Y represents oxygen, $R_1$, represents a saturated hydroxyalkyl radical having from 12 to 20 carbon atoms and $R_2$ represents hydrogen or a saturated alkyl or hydroxyalkyl radical having from 1 to 3 carbon atoms.

27. A composition according to claim 24 wherein said at least one oxazolidinone derivative of formula (I) is selected from 4-(1-hydroxyhexadecyl)-2-oxazolidinone, 4-pentadecyl-5-hydroxymethyl-2-oxazolidinone, 4-(1,2-dihydroxyhexadecyl)-2-oxazolidinone, 4-(1-hydroxypentadecyl)-5-hydroxymethyl-2-oxazolid none and the stereoisomers thereof.

28. A composition according to claim 25 wherein said at least one active agent is selected from active agents having a keratolytic and/or comedolytic property, sunscreens, dyestuffs, preserving agents, surfactants and fragrances.

29. A composition according to claim 25 wherein said at least one active agent is selected from α-hydroxy acids, β-hydroxy acids, α-keto acids, β-keto acids, retinoids, anthralin, anthranoids, peroxides, Minoxidil, antimetabolites, hair tints, hair dyes, perfuming alcoholic solutions, antiperspirants, hair-removing active agents, permanent-waving active agents, depigmenting agents, pigments and chemical screening agents.

30. A composition according to claim 24 wherein said at least one oxazolidinone derivative of formula (I) is present in an amount ranging from 0.05 to 20% by weight relative to the total weight of the composition.

31. A composition according to claim 30 wherein said at least one oxazolidinone derivative of formula (I) is present in an amount ranging from 0.1 to 5% by weight relative to the total weight of the composition.

32. A composition according to claim 25 wherein said at least one active agent is present in an amount ranging from 0.001 to 20% by weight relative to the total weight of the composition.

33. A composition according to claim 24 wherein said composition is in the form of a solution, a gel, a dispersion, an emulsion, a microemulsion or a vesicle dispersion of ionic and/or nonionic type.

34. A composition according to claim 24 wherein said composition is a cleansing, protective, treatment, care or make-up composition for the skin and/or the hair.

35. A process according to claim 1, wherein said composition includes said at least one active agent.

36. A process according to claim 35, wherein said at least one anti-penetrating agent and said at least one active agent are present as separate components of said composition, said separate components being combined together at about the time of application of said composition to said skin, hair, and/or mucous membranes.

* * * * *